United States Patent [19]

Hattori

[11] Patent Number: 4,945,919
[45] Date of Patent: Aug. 7, 1990

[54] RHINOLOGICAL DIAGNOSTIC DEVICE

[75] Inventor: Akira Hattori, Ashiya, Japan

[73] Assignees: Yamaguchi Yakuhin Shokai Ltd., Osaka; Japan Capsular Products, Inc., Tokyo, both of Japan

[21] Appl. No.: 308,769

[22] Filed: Feb. 10, 1989

[51] Int. Cl.$^5$ .............................................. A61B 5/00
[52] U.S. Cl. ................................. 128/736; 128/716; 374/162; 374/186
[58] Field of Search ................. 374/161, 162, 186; 128/716, 736

[56] References Cited

U.S. PATENT DOCUMENTS

| | | | |
|---|---|---|---|
| 3,633,425 | 1/1972 | Sanford | 374/162 |
| 3,720,623 | 3/1973 | Cartmell et al. | 374/161 |
| 3,822,594 | 7/1974 | Parker | 374/161 |
| 3,993,809 | 11/1976 | Schranz et al. | 374/162 |
| 4,682,605 | 7/1987 | Hoffman | 374/162 |

*Primary Examiner*—Francis Jaworski
*Assistant Examiner*—K. M. Pfaffle
*Attorney, Agent, or Firm*—Millen, White & Zelano

[57] ABSTRACT

A rhinological diagnostic device in the form of a multi-layer sheet comprising, from top to bottom, a transparent plastic layer, a thermochromic liquid crystal layer, a black coating layer and a support layer. In use, this multi-layer sheet is positioned beneath the nose to cause expired air from the nostrils to impinge on the transparent plastic layer for diagnosing an abnormality in the nasal cavity based on the resulting topographic color pattern in said thermochromic liquid crystal layer.

3 Claims, 1 Drawing Sheet

RHINOLOGICAL DIAGNOSTIC DEVICE

BACKGROUND OF THE INVENTION

1. Field of the Invention

This invention relates to a rhinological diagnostic device (hereinafter referred to as the nasal test sheet) which is used in diagnosing an inflammation in the nasal cavity or monitoring the degree of healing of the inflammation.

2. Brief Description of the Prior Art

In clinical otorhinology, it is common practice to measure the nasal air flow or the difference in air flow between the right and left nostrils of patients with nasal catarrh, acute rhinitis or other inflammation of the nose. While, for detecting inflammatory lesions in the nasal cavity, nasopharyngoscopy is commonly used to visually examine the nasal meatus and nasopharynx, the nasal air flow is generally measured using the more expedient rhinomanometric device, known as a Gratzel sheet, which is made of glass or stainless steel. Diagnosis using the Gratzel sheet is based on the image of water vapor formed by expired air on the cold surface of the sheet positioned immediately beneath the subject's nose. Though it is thus expedient, the Gratzel sheet has the following disadvantages.

(a) Since glass or stainless steel is high in thermal conductivity, the temperature differential between the sheet and expired air leads to a variation in the amount of water vapor deposited by the expired air.

(b) Since the water vapor deposited on such a rhinomanometric test sheet is dissipated almost instantly irrespective of the ambient atmospheric conditions, an accurate quantitation of such deposits is technically difficult.

(c) The water-vapor image of expired air is not sharp enough and, moreover, disappears in an instant so that it cannot be photographed. It is an object of this invention to provide a nasal test sheet which is free of the above-mentioned disadvantages of the prior art rhinomanometric device and, in addition, has the following novel features.

(a) The temperature of expired air from the subject's nasal cavity which impinges on a thermochromic liquid crystal sheet can be estimated from the color change of the sheet.

(b) The color image produced by expired air on the thermochromic liquid crystal sheet persists for a period of several seconds.

(c) The color image is sharp.

Particularly the feature (a) is quite unique. Thus, it is known that when an inflammation is induced by some cause or other in the human body, the local circulation increases and the inflammation site assumes a temperature higher than that of the surrounding region. In fact, in cases of rhinitis, the temperature of expired air is higher than normal. On the other hand, in allergic rhinitis which has been gathering attention in recent years, curiously the temperature of expired air may be lower than normal dispite the presence of an inflammation. The nasal test sheet of this invention enables the professional measure the temperature of the patient's expired air which could not be ascertained before.

Thus, by utilizing a liquid crystal, the nasal sheet of this invention not only provides an opportunity to determine the temperature of expired air which cannot be known with the conventional rhinomanometric sheet but also provides a visual image of expired air which lasts a sufficient time to permit photographing. These are very remarkable features of this invention.

SUMMARY OF THE INVENTION

This invention relates to a rhinological diagnostic device in the form of a multi-layer sheet comprising, from top to bottom, a transparent plastic layer, a thermochromic liquid crystal layer, a black coating layer and a support layer, said multi-layer sheet to be positioned beneath the nose to permit expired air from the nostrils to impinge on said transparent plastic layer for diagnosing an abnormality in the nasal cavity based on the resulting topographic color pattern in said thermochromic liquid crystal layer.

DETAILED DESCRIPTION OF PREFERRED EMBODIMENTS

Figure 1:
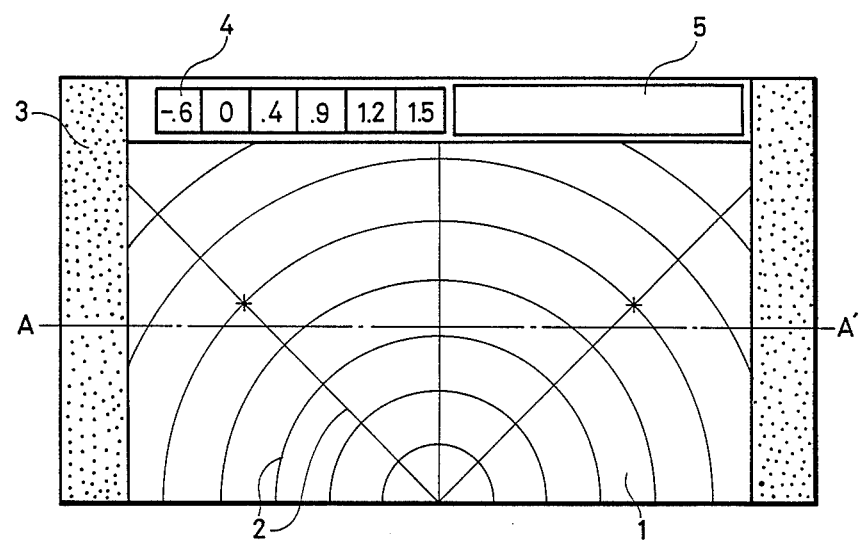
FIG. 1 is a plan view showing the nasal test sheet of this invention.
Figure 2:
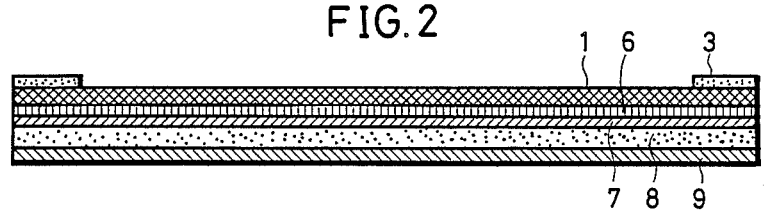
FIG. 2 is a longitudinal section view taken along the line A—A' of FIG. 1.

Referring to FIGS. 1 and 2, the nasal test sheet of this invention comprises, from top to bottom, a top layer (1) of transparent plastic material, a thermochromic liquid crystal layer 6, a bottom layer 7 of black coating material, a heat-insulation layer 8 and a rigid support layer 9. As the material for said thermochromic liquid crystal layer, liquid crystals undergoing changes in color within a given temperature range close to body temperature, specifically in the range of about 28° C. to about 34° C., can be used either singly or in combination. Thus, thermochromic liquid crystals, such as cholesteric liquid crystals, i.e. cholesterol ester derivatives, and chiral nematic liquid crystals which are optically active derivatives of nematic liquid crystals, can be employed with advantage for the purposes of this invention. In preparing the liquid crystal layer 6, the liquid crystal may be used as it is but in consideration of ease of manufacturing and stability, it is preferable to use a microencapsulated liquid crystal.

The thermochromic image of expired air in the liquid crystal layer 6 is quite different from the thermochromic image obtainable with the device used in close contact with the body for the diagnosis of breast cancer, Raynaud's disease, etc. in that the amount of heat storage in said layer 6 is very small and, therefore, the life of the color image is short.

Incidentally, comparison of the thermochromic image produced by contact with the human body with that produced by impinging expired air shows that the time necessary for the onset of thermochromic response is 2 to 3 seconds for the former and less than 1 second for the latter and that the duration of the color image is 6 to 10 seconds for the former and 3 to 4 seconds for the latter. Thus, in the former, it takes some time for the heat to be transferred through protective layers (plastic film, black coating layer and protective layer) to the liquid crystal layer, while, in the latter, the heat is almost immediately transferred to the liquid crystal layer 6 through the plastic layer 1 alone. On the other hand, since the thermal energy of expired air is slight and the amount of heat storage in the liquid crystal layer 6 is also small, the thermochromic image disappears after a brief time as the stored heat is dissipated. To alleviate this drawback, it is particularly preferable to dispose a foamed material, such as foamed polyethylene, polyurethane, polystyrene, polyvinyl chloride or the like, in contact with the reverse side of the heat-responsive liquid crystal sheet.

Instead of using a foamed material for heat insulation, it is possible to apply a foamable material, such as polyurethane, polyvinyl chloride or the like, by coating or spraying and, then, causing it to foam in a later stage.

The surface of the heat-responsive liquid crystal sheet is preferably provided with a scale 2 comprising concentric semi-circlar lines and radial graduations for assisting in the reading of the distance (front) and direction of expired air applied to the nasal test sheet. While, for this purpose, the face or reverse side of the transparent plastic film must be printed, it is preferable to use a white, silver-white or golden printing ink in order that a clear scale pattern may be printed. Moreover, in order that diagnosis will not be interfered with, the line width of the pattern is preferably about 0.03 to 0.1 mm. Furthermore, in order that the nasal test sheet may be repeatedly used in a large number of cases, the surface of the sheet should be wiped clean with ethanol-cotton or gauze after each use. Therefore, the line pattern is preferably printed on the reverse side of the transparent plastic layer 1, that is to say in contact with the surface of liquid crystal layer 6. For the preparation of transparent plastic layer 1 to be used in this invention, such diversified materials as polyethylene terephthalate, polyamide, polyethylene, polypropylene, polystyrene, polyvinyl chloride, polyvinyl alcohol, etc. can be appropriately selected and used. However, in consideration of printing characteristics, strength, rigidity, thermal stability, weather resistance, resistance to organic solvents, etc., polyethylene terephthalate and polyamide films are preferred.

The thickness of transparent plastic layer 1 has a direct bearing on the conduction velocity of the heat of expired air and in consideration of this fact coupled with strength and rigidity factors, it is preferably in the range of about 30 to 100 microns. When the nasal test sheet of this invention is used as supported by the patient's hand, the region of the sheet near the fingers may naturally respond to the body temperature to confound the thermochromic image developed by expired air. Therefore, in order to avoid contact with the fingers, the nasal test sheet is preferably provided with carrying means 3 made of some heat insulation material. Alternatively, the nasal test sheet may be supported on an appropriate stand instead of being supported by hand. The heat insulation material fulfilling the requirements of sufficient heat insulation, resistance to repeated use and sanitation includes, among others, cork, polyethylene foam, rigid plastics such as ABS resin, polymethyl methacrylate, polyamide, polyvinyl chloride, polyester, etc., and polyurethane foam.

To assure the convenience that the expired air temperature of the subject may be immediately ascertained, it is very advantageous to supply the nasal test sheet of this invention together with a table showing the relationship between the temperature and the color of the liquid crystal, i.e. a temperature-color table 4. The numbers affixed to table 4 represent deviations in temperature above or below the normal temperature of expired air, e.g. 30 degrees Celsius, as would be well-known in the art. This temperature-color table 4 is intrinsic to the type and composition of, for example, a cholesteric liquid crystal and is not varied by repeated use. However, it is known that a liquid crystal is degraded by moisture, organic solvents and ultraviolet light. Therefore, the thermochromic response of the liquid crystal layer 6 may fail to conform to the temperature-color table. If the color response of the liquid crystal sheet tends to deviate from the temperature-color correlates given in the table, a degradation of the liquid crystal should be suspected. To ascertain the degree of liquid crystal degradation, it is recommended that the color response be tested using reference temperatures from time to time. From the above consideration, the temperature-color table is preferably attached, through an appropriate support, to the side of the liquid crystal sheet opposite to the side to be set beneath the subject's nose.

In clinical practice, it is desirable to keep a record of the color image developed in the thermochromic liquid crystal layer and, in accordance with this invention, the image can be photographed using a camera and black-and-white or color film. For this purpose, a name plate 5 for writing the subject's name, date of photographying, etc. is preferably disposed adjacent to said temperature-color table. The name plate 5 is preferably a white plastic plate. Then, necessary entry can be made using an aqueous black marking pen and, after photographing, the entry can be erased by wiping with sanitary cotton or gauze.

The nasal test sheet of this invention can be used in the same manner as the conventional Gratzel sheet which is positioned beneath the subject's nose for measuring the nasal air flow. In addition, it enables the doctor or the like to read the temperature of the subject's expired air. The body temperature is known to vary from one individual to another and it is also known that a patient with inflammation in the nasal cavity shows a characteristic expired air temperature. Unlike the conventional Gratzel sheet which only provides information on changes in air flow in the nasal cavity, the nasal test sheet of this invention additionally provides information on the temperature and distribution of expired air which are characteristic of an individual subject and is of great help to the clinical doctor.

In the nasal test sheet of this invention, the liquid crystal displays the temperature distribution of expired air in a thermochromic pattern. The liquid crystal layer which is black before use assumes brown, yellow, red, green and blue colors, for instance, in a sequence from low to high temperature so that the areas of the liquid crystal layer showing such color changes can be topographically ascertained at a glance.

The liquid crystal layer in this invention can be formed in the known manner, selecting the type and composition of liquid crystal according to the desired temperature range. When the nasal test sheet of this invention is put to use, the expired air from the subject's nasal cavity shows delicate changes corresponding to repeated breathing and the color image displayed by the liquid crystal persists for 2 to 5 seconds. Therefore, by photographing the image, a hard record can be obtained for a more accurate diagnosis.

Any thermochromic liquid crystal that has once assumed a color responding to a given temperature loses the color, returning to the most stable condition, upon spontaneous dissipation of heat or quenching. Therefore, the liquid crystal can be repeatedly used to indicate the expired air temperature. This ability to develop colors accurately in response to varying temperatures with good reproducibility is of great importance.

In photographing the thermochromic image produced in the liquid crystal layer with a camera, actuating the stroboscope of the camera may cause a halation which will interfere with formation of a clear picture image.

The problem of halation may be somewhat overcome by selecting the proper position and direction of the stroboscope but in order to obtain a clear picture, it is recommended to matte-finish the transparent plastic layer 1 of the nasal test sheet.

Figure 3:
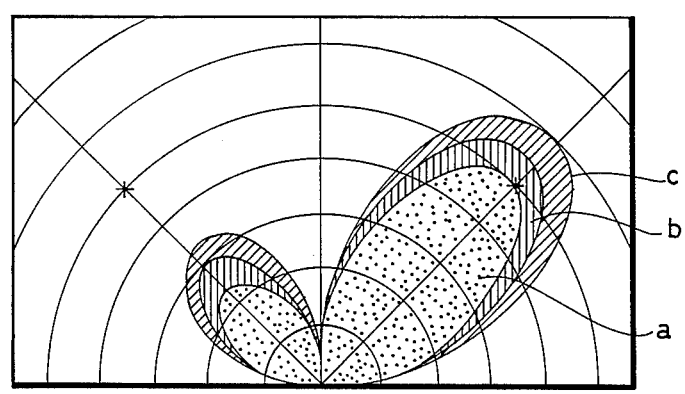
FIG. 3 is an example of application of the nasal test sheet of this invention.

FIG. 3 shows an example of use of the rhinological diagnostic device of this invention. It is seen that the bilateral color images are not identical, indicating clearly that an inflammation exists in the left nostril.

In FIG. 3, a represents a dark blue color which indicates a high temperature area, b a green color indicative of an intermediate temperature area, and c a brown color which stands for a low temperature area. The picture suggests a deformation of the nasal septum and an enlargement of the nasal concha, which can be macroscopically verified. Furthermore, the temperature distribution of expired air from each nostril can be accurately delineated. Thus, the alleviation of fever at an inflammation site with the progress of treatment can be easily monitored by observation of the color image obtainable with the nasal test sheet of this invention.

What is claimed is:

1. A rhinological diagnostic device for diagnosing an abnormality of nasal cavities of a patient which comprises a rigid base plate, a heat insulating layer formed of a foamed plastic material overlying said base plate, a black coating layer covering said heat insulating layer, a thermochromic liquid crystal layer extending over said black coating layer, and a transparent plastic layer covering said liquid crystal layer, said transparent plastic layer and said liquid crystal layer being disposed in heat conductive relationship so that when expired air from the nostrils of said patient is directly applied to said transparent plastic layer, a thermochromic, topographic pattern of said liquid crystal layer is displayed.

2. The rhinological diagnostic device of claim 1, which is provided with a scale for measuring radial distribution of said expired air and colors of said topographic pattern.

3. A rhinological diagnostic device of claim 2 wherein said thermochromic liquid crystal layer consists of microencapsulated cholesteric liquid crystals.

* * * * *